US007001373B2

(12) United States Patent
Clapham et al.

(10) Patent No.: US 7,001,373 B2
(45) Date of Patent: Feb. 21, 2006

(54) INTERFACE FOR LASER EYE SURGERY

(75) Inventors: Terrance N. Clapham, Jamestown, CA (US); Michael Cowperthwaite, Mountain View, CA (US); Richard A. Hofer, Santa Cruz, CA (US); Erik Scramaglia, South San Francisco, CA (US)

(73) Assignee: VISX, Incorporated, Santa Clara, CA (US)

( * ) Notice: Subject to any disclaimer, the term of this patent is extended or adjusted under 35 U.S.C. 154(b) by 309 days.

(21) Appl. No.: 10/227,176

(22) Filed: Aug. 20, 2002

(65) Prior Publication Data

US 2003/0004502 A1    Jan. 2, 2003

Related U.S. Application Data

(62) Division of application No. 09/534,849, filed on Mar. 28, 2000, now Pat. No. 6,558,373.

(60) Provisional application No. 60/128,122, filed on Apr. 7, 1999.

(51) Int. Cl.
*A61F 9/008* (2006.01)
(52) U.S. Cl. ............................................. 606/5; 606/10
(58) Field of Classification Search .................... 606/3, 606/5, 10–13; 602/6
See application file for complete search history.

(56) References Cited

U.S. PATENT DOCUMENTS

| 3,572,913 | A |   | 3/1971  | Korb et al. |
|-----------|---|---|---------|-------------|
| 3,647,287 | A |   | 3/1972  | Schwind     |
| 3,762,404 | A | * | 10/1973 | Sakita ............................ 602/6 |
| 4,579,430 | A |   | 4/1986  | Bille       |
| 4,601,037 | A |   | 7/1986  | McDonald    |
| 4,643,547 | A |   | 2/1987  | Collins et al. |

(Continued)

FOREIGN PATENT DOCUMENTS

AU          8662-414 A      3/1987

(Continued)

OTHER PUBLICATIONS

McDonald, et al. "Myopic Photorefractive Keratectomy: US Experience" In Color Atlas/Text of Excimer Laser Surgery Thompson and McDonnell, Igaku-Shoin New York 1993.*

*Primary Examiner*—David M. Shay
(74) *Attorney, Agent, or Firm*—Townsend and Townsend and Crew LLP; Mark D. Barrish, Esq.

(57) ABSTRACT

A laser surgery system having a computer control system coupled to a laser subsystem and a patient seat. The control system is coupled to the laser through a laser alignment system. The control system can be coupled to the patient seat through a patient alignment system. The control system sends a nominal position signal to move the patient seat, laser subsystem, or both so that the patient's first eye is moved into substantial alignment with the laser beam axis. The control system can send a second nominal signal to move the patient's second eye into substantial alignment with the laser beam axis. The control system can optionally comprise both an operator display and an assistant display. The assistant display provides real-time information to an assistant positioned at an assistant station adjacent the patient seat. The control system can be programmed to display edit fields with different colors to provide an obvious indication of the refractive information of the eye. The control system can comprise an operator input for providing a pre-determined secondary ablative treatment. If it is determined that the first ablative treatment did not completely remove the epithelial layer from a target region, the operator actuates the operator input to deliver the secondary ablative treatment.

19 Claims, 13 Drawing Sheets

U.S. PATENT DOCUMENTS

| | | |
|---|---|---|
| 4,848,340 A | 7/1989 | Bille et al. |
| 4,863,260 A | 9/1989 | Gersten et al. |
| 4,873,623 A | 10/1989 | Lane et al. |
| 4,885,998 A | 12/1989 | Span et al. |
| 4,967,381 A | 10/1990 | Lane et al. |
| 5,009,498 A | 4/1991 | Gersten et al. |
| 5,098,426 A | 3/1992 | Sklar et al. |
| 5,125,731 A | 6/1992 | Fiorini et al. |
| 5,219,343 A | 6/1993 | L'Esperance, Jr. |
| 5,220,360 A | 6/1993 | Verdooner et al. |
| 5,349,398 A | 9/1994 | Koester |
| 5,356,409 A | 10/1994 | Nizzola |
| 5,416,539 A | 5/1995 | Gersten et al. |
| 5,423,801 A | 6/1995 | Marshall et al. |
| 5,445,633 A | 8/1995 | Nakamura et al. |
| 5,455,766 A | 10/1995 | Scheller et al. |
| 5,481,936 A | 1/1996 | Yanagisawa |
| 5,488,443 A | 1/1996 | Ota et al. |
| 5,505,724 A | 4/1996 | Steinert |
| 5,526,073 A | 6/1996 | Mattioli |
| 5,526,812 A | 6/1996 | Dumoulin et al. |
| 5,620,436 A | 4/1997 | Lang et al. |
| 5,634,920 A | 6/1997 | Hohla |
| 5,634,921 A | 6/1997 | Hood et al. |
| 5,684,562 A | 11/1997 | Fujieda |
| 5,686,981 A | 11/1997 | Anan et al. |
| 5,749,871 A | 5/1998 | Hood et al. |
| 5,765,910 A | 6/1998 | Larkin et al. |
| 5,782,822 A | 7/1998 | Telfair et al. |
| 5,836,872 A | 11/1998 | Kenet et al. |
| 5,841,511 A | 11/1998 | D'Souza et al. |
| 5,843,070 A | 12/1998 | Cambier et al. |
| 6,106,513 A * | 8/2000 | McMillen et al. .............. 606/4 |

FOREIGN PATENT DOCUMENTS

| | | | |
|---|---|---|---|
| WO | 0 224 322 A1 | 6/1987 | |
| WO | 9746784 | * 12/1997 | .................... 606/5 |

* cited by examiner

INTERFACE FOR LASER EYE SURGERY

CROSS-REFERENCES TO RELATED APPLICATIONS

The present application is a divisional of and claims the benefit from U.S. patent application Ser. No. 09/534,849, filed Mar. 28, 2000, now U.S. Pat. No. 6,558,373 which claims benefit of U.S. Provisional Patent Application No. 60/128,122, filed Apr. 7, 1999, under 37 C.F.R. §1.78, the complete disclosure of which are incorporated herein by reference for all purposes.

STATEMENT AS TO RIGHTS TO INVENTIONS MADE UNDER FEDERALLY SPONSORED RESEARCH OR DEVELOPMENT

Not Applicable

REFERENCE TO A "SEQUENCE LISTING," A TABLE, OR A COMPUTER PROGRAM LISTING APPENDIX SUBMITTED ON A COMPACT DISK

Not Applicable

BACKGROUND OF THE INVENTION

The present invention relates generally to methods, systems and devices for performing corrective eye surgery. More particularly, the present invention relates to improved computer and laser system interface methods, computer interface programs, and operator system interfaces. The present invention is particularly useful for enhancing the speed, ease, safety, and efficacy of laser eye surgical procedures such as photorefractive keratectomy (PRK), laser in situ keratomileusis (LASIK), and the like.

Laser eye procedures typically employ ultraviolet or infrared lasers to remove a microscopic layer of stromal tissue from the cornea to alter its refractive power. Excimer lasers (i.e. ultraviolet laser), such as the VISX STAR™ or STAR S2™ laser system, use argon and fluorine gas to create a non-thermal laser light to break molecular bonds, in a process known as photoablation. Ultraviolet laser ablation results in the photodecomposition of the corneal tissue, but generally does not cause significant thermal damage to adjacent and underlying tissues of the eye. The photoablation removes stromal tissue to change the contour of the cornea to correct myopia (near-sightedness), hyperopia (far-sightedness), and astigmatism.

In general, existing laser eye surgery systems have included an operator interface for use by the laser system operator in setting-up, controlling, monitoring, and generally directing the laser treatment of the patient's eyes. The safety and efficacy of a photorefractive procedure depends in part on the operator's ability to interact with the laser control system using the operator interface. The costs of each surgical procedure are significantly affected by any unnecessary time delays in setting-up or directing the procedure. Unfortunately, existing operator interfaces are less than ideal in a number of aspects.

The photoablation of corneal tissues benefits from precise alignment between the eye and a therapeutic laser. Known laser eye surgical alignment systems typically have a patient seat or bed with the patient seated, lying down, or reclined in a supine position. To align the patient with the laser beam, the operator must manually adjust the seat or bed into alignment with the laser. Additionally, because the seat or bed often has limited speeds and/or ranges of motion the alignment procedure can be quite time consuming—especially when both eyes are to be treated.

Known operator interface display systems also suffer from a variety of additional disadvantages. For example, it may not always be as clear as would be desirable what type of refractive error and/or correction is represented on a controller display. Specifically, hyperopia and myopia designate alternative refractive errors which are opposite in nature, but it may not always be clear whether a negative value in a hyperopic display field designates a myopic characteristic or correction or a hyperopic characteristic or correction. An error introduced at this point would result in the patient's refractive error being doubled instead of corrected.

Laser ablation of the epithelial layer, an outer layer of the eye, is often performed before the re-sculpting ablation begins. While these epithelial ablations are now controlled from the operator interface, it can be time consuming to reconfigure the system if the epithelial layer is not completely removed from with the initial laser ablation treatment. Finally, known laser refractive surgery systems do not always provide sufficient information to everyone involved in the procedure. In addition to the system operator, the patient and assistant might benefit from procedure and/or system information which is currently directed only to the operator. These limitations detract from the speed, safety, and comfort of known refractive surgical techniques.

For these reasons, it is desired to provide an improved interface for laser eye surgery. In particular, it is desired to have a system capable of automatically aligning the patient's eye with the laser. Furthermore, it would be desirable to have a system which quickly and automatically aligns the patient's second eye after the first eye has been treated. It is also desired to have a system interface which would allow the operator to easily determine the refractive characteristics that have been entered. It would further be desirable to provide a system in which the assistant can view system information regarding the procedure, while still being near the patient. It would further be desirable if such a system could easily control the complete ablation of the target portion of the epithelial layer. At least some of these objectives will be met by the system and method of the present invention described hereinafter and in the claims.

BRIEF SUMMARY OF THE INVENTION

The present invention generally provides improved laser eye surgery devices, systems, and methods. The invention generally enhances laser eye treatment by using methods and interfaces which increase treatment efficiency and provide improved system features.

In one aspect, the present invention provides a laser refractive surgery system having a laser that produces a laser beam. The laser defines a longitudinal axis along the path of the laser beam. A patient seat is movable along at least the X and Y horizontal directions. A control system is coupled to the patient seat and laser and automatically positions the seat at a nominal position. At the nominal position, the seat substantially aligns a patient's first eye with the laser axis. In a particular embodiment, the control system can be adapted to automatically substantially align a second eye with the laser axis.

In another aspect, the present invention provides a laser refractive system having a laser which produces a laser beam that defines a longitudinal axis. A patient seat or bed is contoured to support a patient in a patient position so that first and second eyes of the patient are near first and second nominal axes, respectively. A seat alignment system couples the seat to the laser. The patient alignment system moves the seat, the laser, or both, in response to a nominal position signal so that the beam axis is aligned with the first optical axis.

In yet another aspect, the present invention provides a method for positioning a patient for refractive eye surgery. The method includes the steps of automatically positioning a patient in a first nominal position. In the first nominal position, the patient's first eye is substantially aligned with a laser. The patient is then automatically positioned to a second nominal position. In the second nominal position, the patient's second eye is substantially aligned with the laser. In most embodiments, the patient is automatically moved to the second nominal position after the first eye has been treated.

In another aspect, the present invention provides a method for aligning a patient for laser surgery. The method comprises placing a seat in a patient loading position. A control system is activated to move the seat to a first nominal position in which the patient's eye is substantially aligned with a laser beam axis.

In a further aspect, the present invention provides a laser eye surgery system. The system includes a laser for producing a laser beam. A patient seat or bed is positioned adjacent the laser. A control system is coupled to the laser. The control system has laser operation controls and displays information about the treatment. An assistant display is coupled to the control system, wherein the monitor is viewable from adjacent the patient seat or bed so an assistant can monitor the treatment from the assistant station.

In another aspect, the present invention provides a method of providing treatment information of a laser eye procedure to an operator and an assistant adjacent a patient. The method comprises monitoring treatment information of a laser eye procedure. The treatment information is displayed in real-time on a computer control system and an assistant display. The assistant display screen is aligned substantially orthogonal to the computer control system so the assistant adjacent the patient can view the information displayed on the assistant display.

In yet another aspect, the present invention provides a method for performing corrective eye treatment. The method includes the step of directing a laser beam at a corneal region of an eye of a patient. Information about the treatment is displayed to the operator in real-time on a control station display. Information about the treatment is also displayed to an assistant in real-time on an assistant display, such that the assistant can view the information while adjacent the patient.

In a further aspect, the present invention provides a laser eye surgery system having a laser system for producing a laser beam for refractive surgery on a cornea. A computer control station, having an operator interface and control system, is coupled to the laser system to monitor and control the laser system. Typically, the computer control system is adapted to display on the operator interface a first color with fields displaying myopic refractive information and a second color with fields having hyperopic refractive information. The first color and second color are preferably different colors.

In another aspect, the present invention provides a method of displaying refractive information. The method includes the step displaying refractive information on an edit field. A first background color is provided for the edit fields displaying myopic refractive information. A second background color is provided for the edit fields displaying hyperopic refractive information.

In yet another aspect, the present invention provides a system for removing an epithelial layer from a target region in a cornea during photorefractive surgery. The system includes a laser which produces a tissue-ablative beam. The laser provides an initial uniform epithelial ablative treatment over the region and a refraction altering re-sculpting ablative treatment. A control system that is adapted to monitor and control the ablative treatments is coupled to the laser. An operator input is coupled to the control system, such that upon actuation of the operator input, the control system actuates the laser to provide an incremental epithelial ablative treatment.

In a further aspect, the present invention provides a system for removing an epithelial layer from a target region in a cornea. The system includes a laser which provides a first ablative treatment and a secondary ablative treatment. A control system is coupled to the laser and is adapted to monitor and control the tissue ablative treatments. An operator input for providing a secondary ablative treatment is coupled to the control system. Upon actuation of the operator input, the laser provides a secondary ablative treatment. In a preferred embodiment, the operator input comprises a button mounted to the control system. Actuation of the button can deliver a pre-determined amount of the tissue ablative beam.

In yet another aspect, the present invention provides a method for removing an epithelial layer from over a stromal layer in a cornea. The method includes irradiating a target region of the epithelial layer with a first amount of ablative radiation. If it is determined that the first amount of ablative radiation did not completely remove the epithelial layer from the target region, the target region of the epithelial layer is irradiated with a predetermined secondary amount of ablative radiation. In a preferred embodiment, a button is depressed to deliver the secondary amount of ablative radiation.

These and other aspects of the invention will be further evident from the attached drawings and description of the invention.

DETAILED DESCRIPTION OF THE INVENTION

The present invention provides systems, methods and interfaces for improving the laser treatment of the eye. More specifically, the systems and interfaces of the present invention are particularly suited for use on the STAR™ and STAR S2™ Excimer Laser System which are commercially available from VISX, Incorporated of Santa Clara, Calif. Additionally, the systems and interfaces of the present invention are suitable for use with laser systems manufactured by Chiron Vision of Irvine Calif., Summit Technology of Watertown, Mass., Nidek Co., Ltd. of Gamagori, Japan, Meditec of Heroldsberg, Germany, LaserSight of Orlando, Fla., Autonomous Technologies Corporation of Orlando, Fla., and the like. The systems may be programmed to perform the methods of the present invention by providing a computer program in the form of a tangible medium comprising computer readable code setting further the methods described in more detail below.

Figure 1:
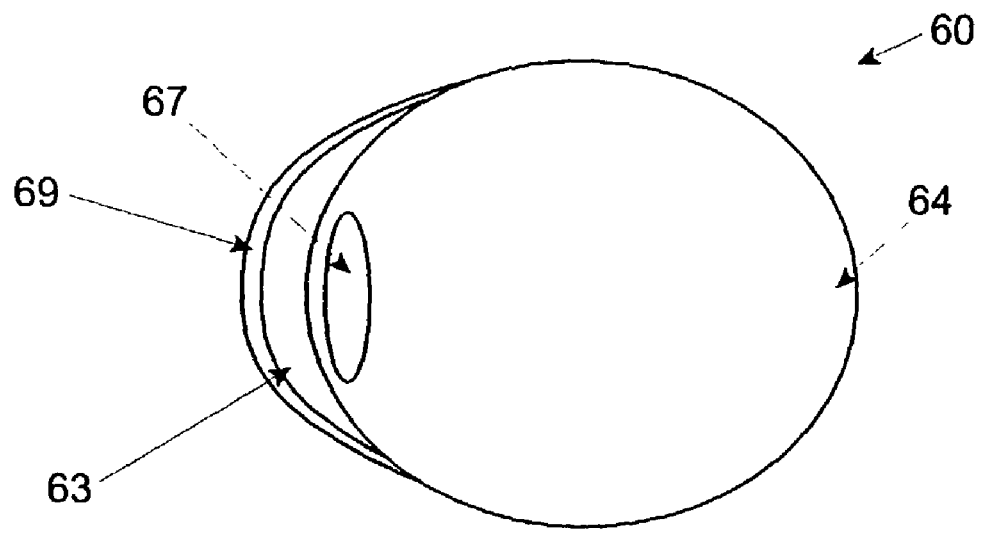
FIG. 1 illustrates a simplified cross-sectional view of a human eye.

FIG. 1 illustrates a simplified view of an eye. The cornea 69 covers the pupil and provides the focusing power to the eye. The pupil 63 is located behind the cornea and controls the amount of light entering the eye. The lens 67 is a clear structure located behind the cornea and provides fine-tuning for focusing. The retina 64 transmits the images to the brain. Myopia occurs when the eye is too long for the cornea's curvature. Light rays entering the eye do not come to a sharp focus on the retina, but instead focus further forward of the retina. In contrast, hyperopia occurs when the eye is too short for the cornea's curvature and light rays entering the eye focus behind the retina.

Figure 2:
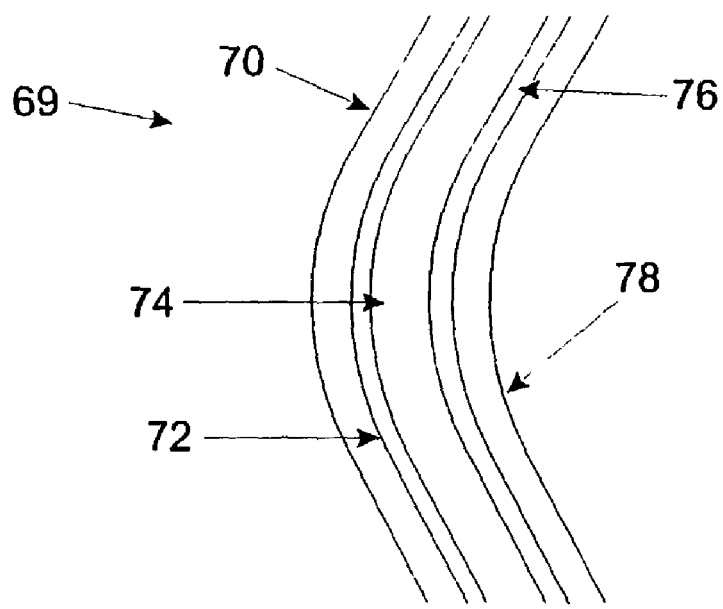
FIG. 2 illustrates a cross-sectional view of the five layers of the cornea.

Specifically, as shown in FIG. 2, the cornea is composed of five layers of tissue. The cornea is comprised of the epithelial layer 70, the lamina limitans anterior (also known as Bowman's layer 72), the stromal layer 74, lamina limitans posterior (also known as Descemet's layer 76), and the endothelium 78. The outermost layer, the epithelial layer 70 is approximately 50 $\mu$m thick. For patients undergoing a photorefractive keratectomy (PRK), the epithelial layer of a target region is removed or displaced from over the pupil before the stromal layer 74 is shaped to correct the contour of the cornea.

Figure 3:
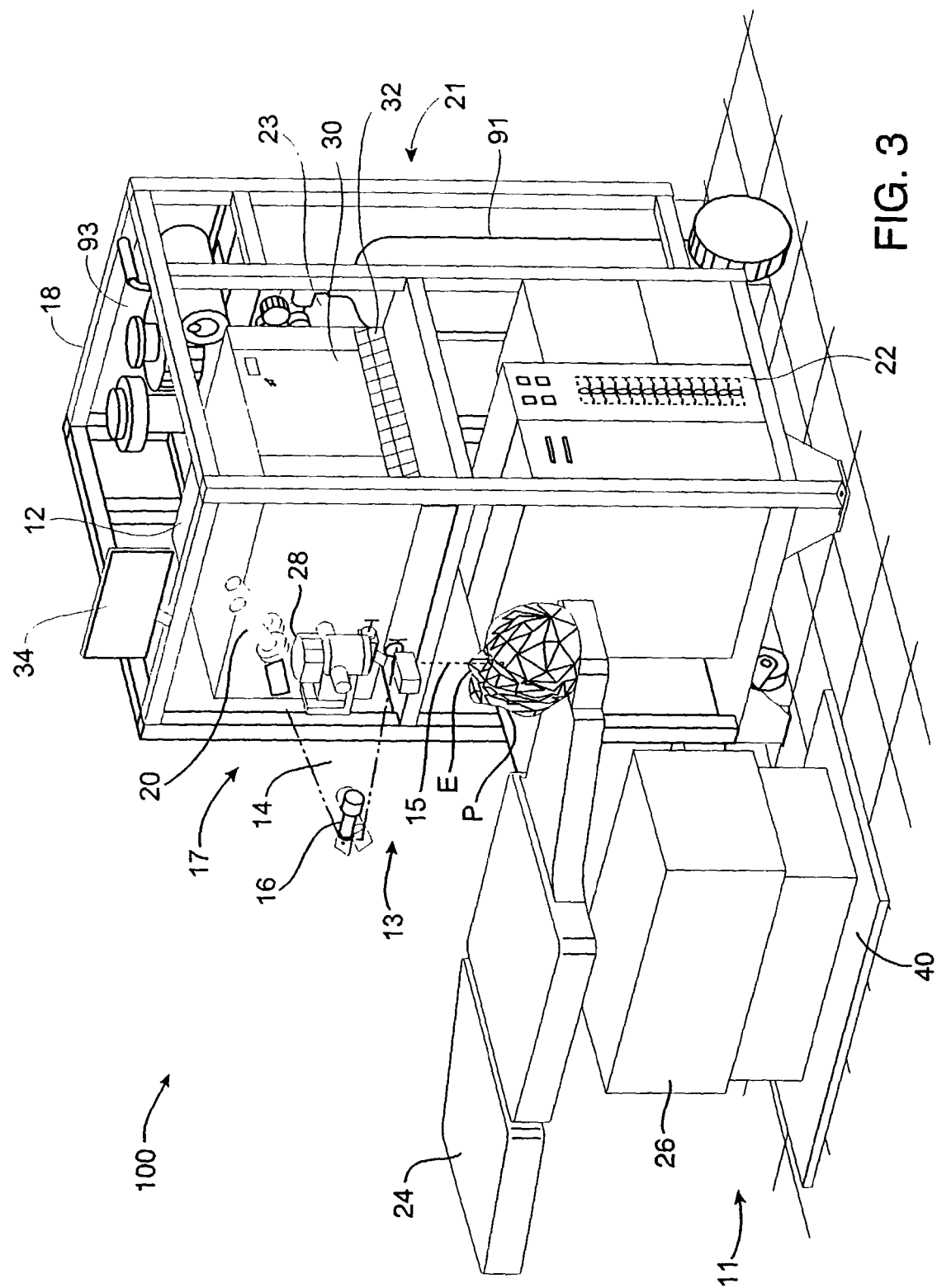
FIG. 3 illustrates a perspective view of a laser eye surgery system in accordance with the principles of the present invention.

FIG. 3 illustrates a laser surgery system embodiment in accordance with the principles of the invention. Laser eye surgery system 100 is designed for performing corrective laser surgery with an excimer laser to reshape the surface of the cornea to correct refractive vision errors. In general, the surgery system of the present invention includes an operator control station 21 having a computer control system 22 and laser operation controls 23. The computer control system 22 generally comprises a conventional PC computer coupled to a keyboard 32, an operator display 30, an assistant display 34, and standard computer input and subsystem components (e.g., flexible and hard disk drives, CD-ROM, an internet connection, modem, memory boards and the like). Various input devices, such as a touch screen, joystick, mouse, foot pedals, and the like, can be used to input information or send control signals to the control system. Such input devices will often be used to download and execute a computer code from a tangible storage media, such as a computer program in the form of a computer-readable floppy disk, a CD-ROM, a cartridge, a data tape, or other conventional medium, to embody the methods of the present invention. Additionally, the computer 22 can be programmed using any conventional programming technique to encode the methods for the present inventions, as described in more detail below. Further details of suitable system for performing a laser ablation procedure can be found in commonly assigned U.S. Pat. Nos. 4,665,913, 4,669,466, 4,732,148, 4,770,172, 4,773,414, 5,207,668, 5,108,388, 5,735,843, 5,711,762, 5,219,343, 5,646,791 and 5,163,934, the complete disclosures of which are hereby incorporated by reference.

The computer control system 22 is typically mounted to a base frame 18 and is preferably coupled to a laser subsystem 13 through a laser alignment system 17. Additionally, the computer control system is coupled to a patient seat 24 through a patient alignment system 11. As will be described more fully below, the patient seat 24, laser delivery optics 16, or both, can be moved in response to a control signal to align the patient's eye E with a laser beam axis 15.

Figure 4:
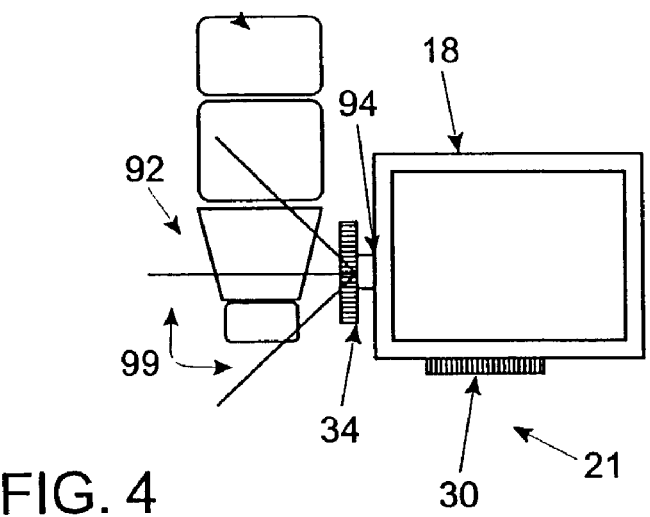
FIG. 4 illustrates a plan view of the system of FIG. 1 showing the relative orientation of the assistant display and the operator display.

The operator interface display 23 and the assistant display 34 are typically conventional computer monitors. However, the operator display and assistant display can be a touch screen, a computer controlled timer, an alphanumeric light emitting diode (LED), liquid crystal display, or the like. The assistant display 34 is used to provide real-time visual indication to the assistant or observer of the remaining treatment time or other information associated with the laser treatment. Preferably, the assistant display is a dedicated monitor mounted on the arm supporting a laser delivery optics 16 or base frame 18 (FIG. 4). However, as shown in FIG. 3, the assistant display can be mounted anywhere that allows the assistant or observer to view the information shown on the assistant display while adjacent the patient.

Figure 4A:
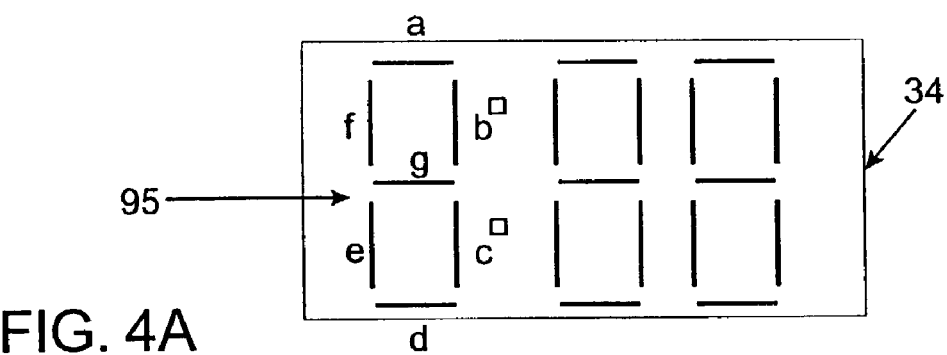
FIG. 4A illustrates an embodiment of the assistant display.
Figure 4B:
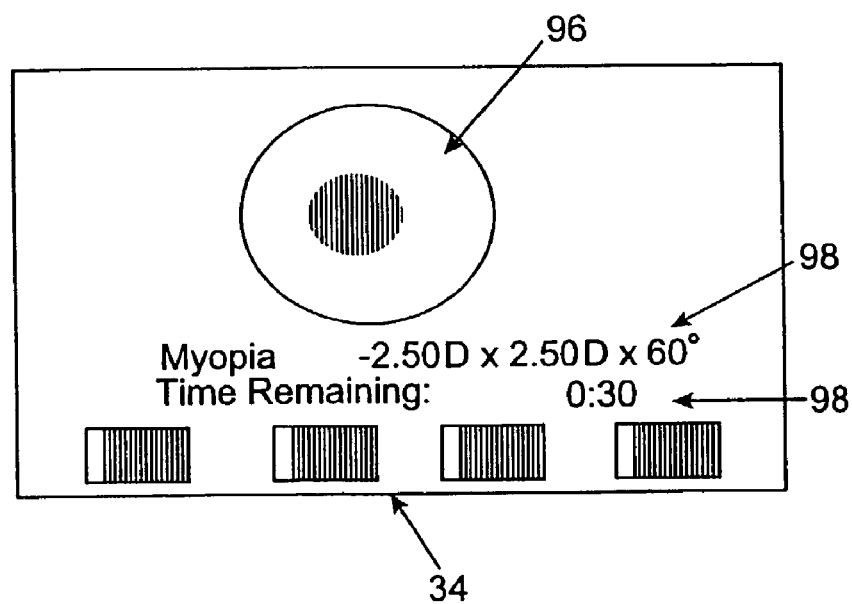
FIG. 4B illustrates another embodiment of the assistant display.

As illustrated in FIG. 4, the assistant display 34 is typically mounted on arm 94 and aligned orthogonal to the operator interface 30. Preferably, the assistant display faces toward the patient seat 24, where the assistant station 92 is typically located. The assistant display typically shows the remaining time in characters which are approximately 20 mm in height. The assistant display preferably has at least a +/−50° viewing angle 99, but the viewing angle will vary depending on the type of display used and the placement of the assistant display. In some embodiments, the assistant display is rotatable and/or movable to a different viewing position. A plurality of assistant displays can be coupled to the computer to allow multiple observers to view the treatment. For example as illustrated in FIGS. 4A and 4B, a first assistant display can be programmed to show the time remaining until completion of the procedure 95, while a second assistant display can be programmed to show a virtual reticle 96, the refractive information 98, or current depth of the ablation (not shown). It should be appreciated that the control system can be configured to display a variety of information on the assistant display 34 and the operator display 23. The displays can display the same information, different information or any combination thereof.

One embodiment of the assistant display employs a method of decoding Binary Code Decimal (BCD) into Seven-Segment Code. The decoder is a combinational circuit that accepts a decimal digit in BCD and generates the outputs for selection of segments that display the decimal digit. Each digit of the display is formed from seven segments (a, b, c, d, e, f, g), each consisting of one light emitting diode (LED) that can be illuminated by digital signals. The numeric designation chosen to represent the decimal digits is shown in FIG. 4A. The decoding is performed inside a programmed logic device (PLD).

Figure 5A:
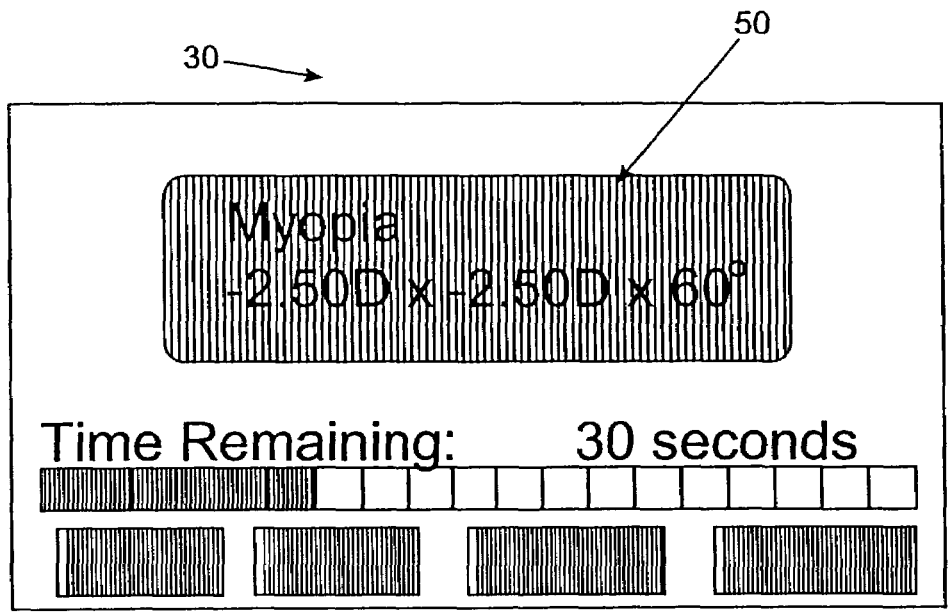
FIG. 5A illustrates an interface display having a first background color for a screen displaying myopic refractive information.
Figure 5B:
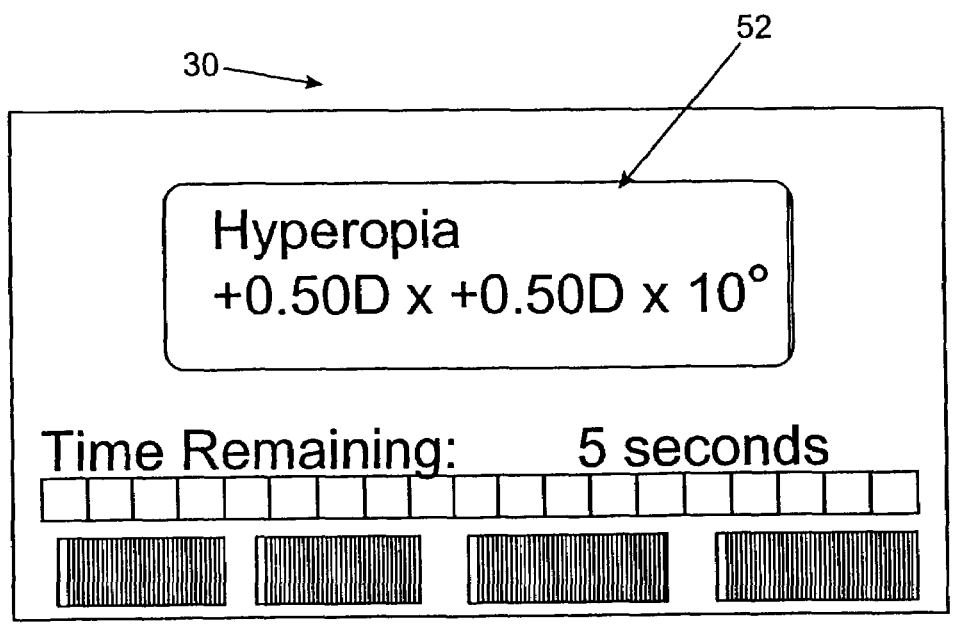
FIG. 5B illustrates an interface display having a second background color for a screen displaying hyperopic refractive information.

Referring now to FIGS. 5A and 5B, the computer control system 22 can be programmed to contain edit fields on the operator interface display 30 for entering and/or displaying refractive information of the patient's eye. The control system can be programmed to display the edit fields with different colors to provide a display which provides an obvious indication of the refractive information of the eye. The edit fields of the system preferably change color to reflect the change in sign (negative or positive) of the values that are displayed in the edit field. Edit fields containing myopic refractive values can have a first color 50, while edit fields containing hyperopic refractive information can have a second color 52. Because myopic refractive information has traditionally been associated with the color red, edit fields having myopic or negative refractive information preferably have a red background. Conversely, edit fields having hyperopic or positive refractive information preferably have a black background. However, it is contemplated that any combination of background colors can be used to display the refractive information. Additionally, instead of having a different background colors, the control system can be programmed to provide different font colors. In most cases, the refractive information will still have the preceding "+" or "−" in addition to the different colored backgrounds or fonts.

The combination of the different colors and leading sign allows the operator to easily determine, at a glance, whether the refractive information is myopic or hyperopic, and will allow the operator to alter or stop the treatment if desired. For example, as illustrated in FIG. 5A, for an eye having mild myopia with a correction of −2.50 diopters the background on an operator display 30 will be a first color 50. As shown in FIG. 5B, if the refractive property of the eye is corrected to +0.50 diopters, the background will change to a second color 52.

Another aspect of the present invention is the addition of an operator input which provides a pre-determined secondary ablative treatment of the epithelial layer. The improved operator interface preferably supports the "no-touch PRK," which removes the epithelial layer with a laser instead of a mechanical scrubber or spatula. In order to assure uniform removal of the epithelial layer over the entire target region, the ablative radiation is typically patterned or adjusted by the control system, as described in U.S. patent application Ser. No. 09/022,774, filed Feb. 2, 1998, the full disclosure of which is incorporated herein by reference. However, even with a patterned laser, the first ablative treatment often does not completely remove the epithelial layer from the target region.

Figure 6:
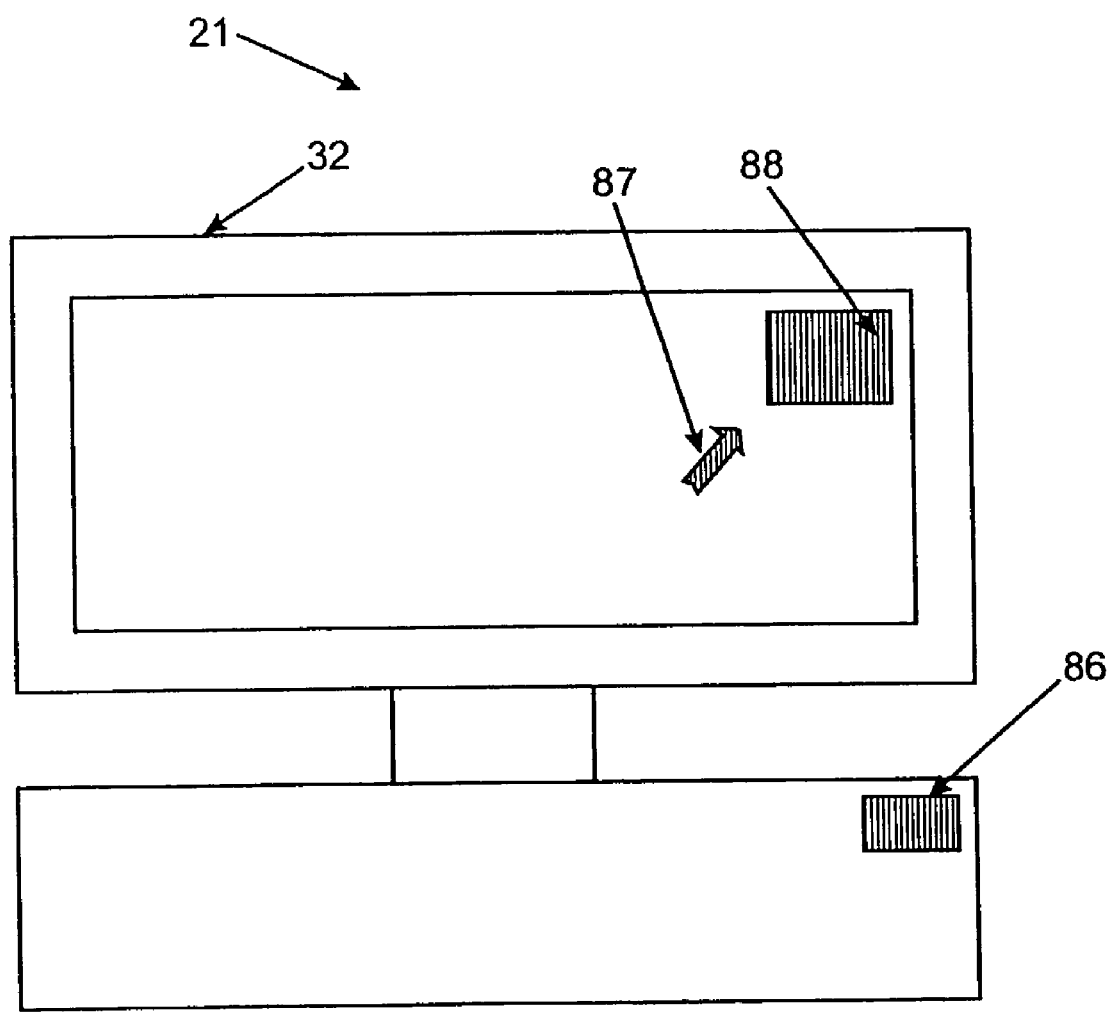
FIG. 6 illustrates a control station having a physical button and a button actuatable by a cursor.
Figure 7:
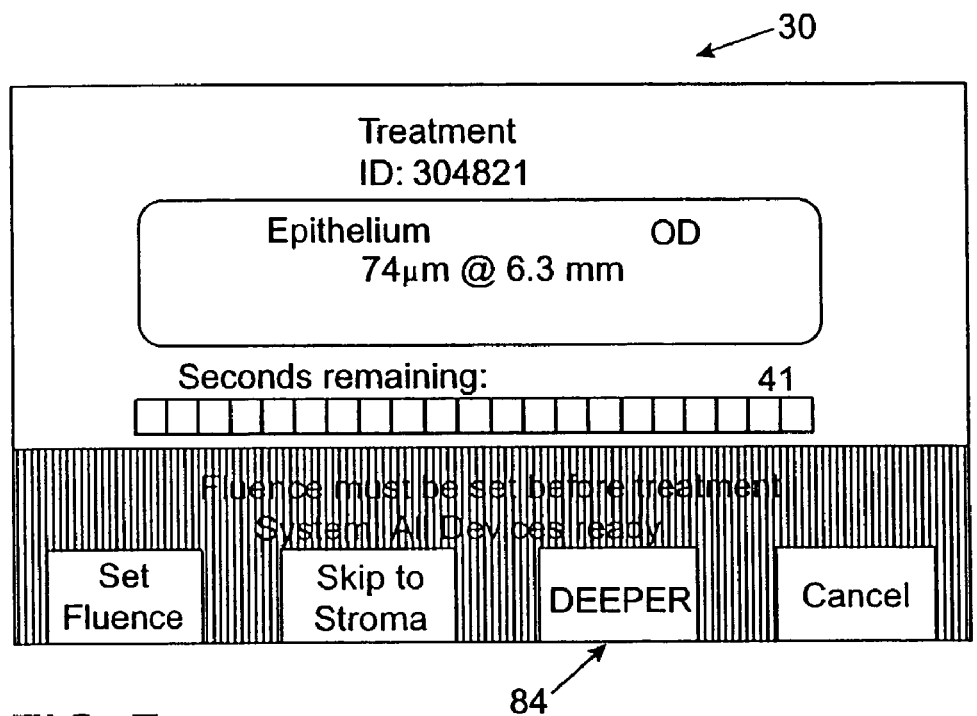
FIG. 7 shows a touch screen having a sample treatment screen with a "deeper button" to incrementally ablate corneal tissue to complete removal of the epithelium in preparation for a re-sculpting procedure.

The control system can be programmed to deliver a pre-determined first amount of ablative energy and a pre-determined secondary ablative treatment. In most embodiments, the secondary ablative treatment is an incremental or smaller dosage of the first ablative treatment. Preferably, the secondary ablative treatment is delivered through actuation of a "deeper" button at the control station 21. As illustrated in FIGS. 6 and 7, the button can be a physical button 86, an icon 88 actuatable by a computer cursor 87, a button 84 on a touch screen, or the like. As will be described more fully below, actuation of the deeper button delivers a secondary ablative treatment without requiring the physician to reprogram the laser. Once it is determined that the epithelial layer has been completely ablated from the target region, the laser can proceed to the shaping of the stromal layer.

Referring again to FIG. 3, the control system 22 is typically coupled to the laser subsystem 13 to control the treatment of the cornea. Laser 12 is optically coupled to laser delivery optics 16, which direct laser beam 14 along a laser axis 15 to an eye of a patient P. Laser 12 can produce a single beam or multiple scanning beams of ablative radiation. A delivery optics support structure (not shown) extends from a base frame 18 to support the laser. Laser 12 generally comprises an excimer laser, ideally comprising an argon-fluorine laser producing pulses of laser light having a wavelength of approximately 193 nm. An excimer laser is the illustrative source of an ablating beam, however, other lasers, such as solid state lasers, are equally suitable in the present invention. The laser system may include a variety of solid state lasers, including frequency multiplied solid state lasers such as flash-lamp and diode pumped solid state lasers. Exemplary solid state lasers include UV solid state lasers (approximately 193–215 nm) such as those disclosed in U.S. Pat. Nos. 5,144,630, 5,742,626, Borsuztky et al., "Tunable UV Radiation at Short Wavelengths (188–240 nm) Generated by Sum Frequency Mixing in Lithium Borate", Appl. Phys. 61:529–532 (1995), the full disclosures of which are incorporated herein by reference. Such lasers include, but are not limited to, alternative lasers providing ultraviolet radiation, for example, solid state lasers, including frequency multiplied solid state lasers such as flash-lamp and diode pumped solid state lasers, including UV solid state lasers (approximately 193–215 nm) such as those disclosed in U.S. Pat. Nos. 5,144,630, 5,742,626, Borsuztky et al., "Tunable UV Radiation at Short Wavelengths (188–240 nm) generated by Sum Frequency Mixing in Lithium Borate," Appl. Phys. 61:529–532 (1995), the full disclosures of which are incorporated by reference. Laser 12 will preferably be designed to provide feedback stabilized fluence of 160 mJoules/cm$^2$ at the patient's eye, as delivered via delivery optics. The system may be used with alternative sources of radiation of any wavelength, particularly those adapted to controllably photo-decompose the corneal tissue without causing significant damage to adjacent and/or underlying tissues of the eye. Laser 12 and delivery optics 16 will generally direct laser beam 14 to the eye of patient P under the direction of a computer 22. Computer control system 22 will generally selectively expose portions of the cornea to laser pulses of laser beam 14 to remove the epithelial layer of the target region and to effect re-sculpting of the cornea and later the refractive characteristics of the eye. A microscope 20 mounted on the delivery optic support structure near the control system and above the patient's head P, allows the operator to monitor the progress of the treatment. Other ancillary components of the laser subsystem 13 include a patient eye retention system (not shown), an ablation effluent evacuator/filter 91, as well as the gas delivery system 93.

Laser beam 14 may be tailored to produce the desired re-sculpting using one or more variable apertures (such as a variable iris and variable width slit as described in U.S. Pat. Nos. 5,713,892, 5,711,762 and 5,735,843 the full disclosures of which are incorporated herein by reference), by varying the size and offset of the laser spot from the axis of the eye (as described in U.S. Pat. No. 5,683,379, and also described in co-pending U.S. patent application Ser. No. 08/968,380, filed Nov. 12, 1997, the full disclosures of which are incorporated herein by reference), by scanning the laser beam over the surface of the eye and controlling the number pulses and/or dwell time (as described by U.S. Pat. No. 4,665,913, the full disclosure of which is incorporated herein by reference), using masks in the optical path of laser beam 14 which ablate to varying the profile of the beam incident on the cornea (as described by U.S. patent application Ser. No. 08/468,895, filed Jun. 6, 1995, the fill disclosure of which is incorporated herein by reference), or the like. The computer programs and control methodology for each of these re-sculpting techniques is well described in the patent literature. Additional optical components may also be included in the optical path of laser beam 14, such as integrators to spatially and/or temporally control the distribution of energy within the laser beam (as described in U.S. Pat. No. 5,646,791, the disclosure of which is incorporated herein by reference), and the like.

Referring again to FIG. 3, computer control system 22 is preferably coupled to both a patient alignment system 11 and a laser alignment system 17 to align the laser beam axis with a first optical axis of a first eye. The head of patient P can be firmly supported on and preferably restrained by a contoured patient seat 24 to support a patient in position so that first and second eyes of the patient are near first and second nominal optical axes.

Positioning of the eye E relative to the laser delivery optics is generally effected by movement of the patient seat 24 into substantial alignment with the laser beam axis 15. The patient is generally laying down or reclined in a supine position. However, in alternative embodiments the patient is oriented in an upright seated position (as described in U.S. Pat. No. 5,795,351, the full disclosure of which is incorporated herein by reference).

Patient alignment system 11 preferably comprises a gross adjustment mechanism 26 having an activating motors to move the seat or bed in the X, Y and Z direction. The gross adjustment mechanism structurally couples the seat to the laser and can be actuated by a signal from the control system or manually actuated by a joystick 25 to move the patient seat along at least the X and Y horizontal directions to align the patient's eye with the laser beam axis (FIG. 7A).

The optical system and/or the laser delivery optics 16 can be moved with a fine adjustment mechanism 28 of the laser alignment system 17 to align the laser beam axis 15 with the first optical axis 80 while the patient is supported on the patient seat. If the laser delivery optics are to be moved, the objective lens of the microscope will preferably remain affixed relative to at least a portion of the laser optical train adjacent the eye so as to maintain alignment between the microscope field of view and the laser treatment site, as described in co-pending U.S. patent application Ser. No. 09/105,073, filed Jun. 26, 1998, the full disclosure of which is incorporated herein by reference. The fine adjustment mechanism 28 can be manually actuated or computer actuated to finely move the laser delivery system to fully align the eye with the laser beam (FIG. 3). Typically, the fine adjustment mechanism is comprised of an activating motor which can move the laser delivery optics in the X, Y, and Z direction. Typically, the fine adjustment mechanism uses the same joystick and moves the laser optics at a slower speed. In alternative embodiments, the fine adjustment mechanism can be coupled to the patient seat to finely align the patient's eye with the laser by making minute adjustments to the seat. Preferably, when the fine adjustment is coupled to the seat, the same joystick and activating motor are used, but the motor is adapted to move at a lower speed.

Figure 7A:
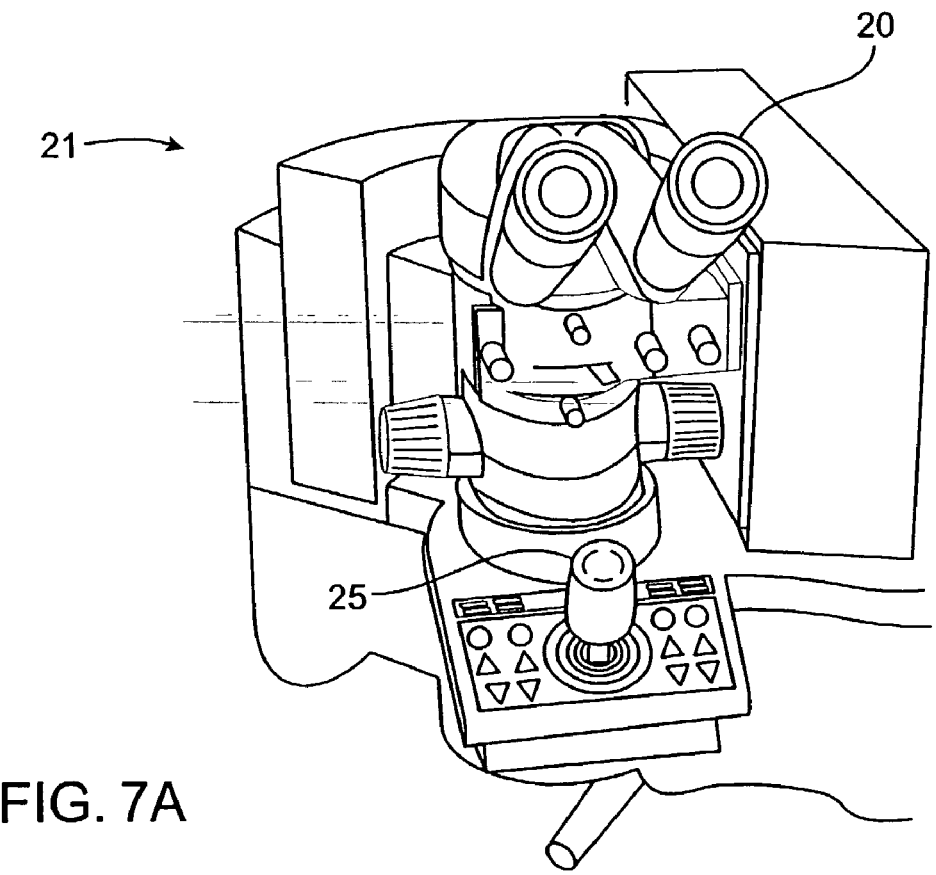
FIG. 7A illustrates a joystick setup which can control the gross adjustment mechanism and/or the fine adjustment mechanism.

FIG. 7A illustrates a typical joystick setup. Preferably, the joystick 25 is located at the operator's station 21 and adjacent the microscope 20. The joystick adjusts the position and orientation of the patient chair and/or the laser optics. Typically, movement of the joystick is progressive, i.e., the farther the joystick is moved from the rest position, the faster the chair moves. In a preferred setup, movement of the joystick to the left causes the patient chair to move to the right, and vice versa. Movement of the joystick forward moves the patient toward the operator, and vice versa. Turning of the joystick handle clockwise can move the patient chair upward and vice versa. However, alternative setups are equally suitable in the present invention. For example, an alternative setup can include moving the joystick to the left to move the patient to the left and moving the joystick forward to move the patient away from the operator.

Figure 8A:
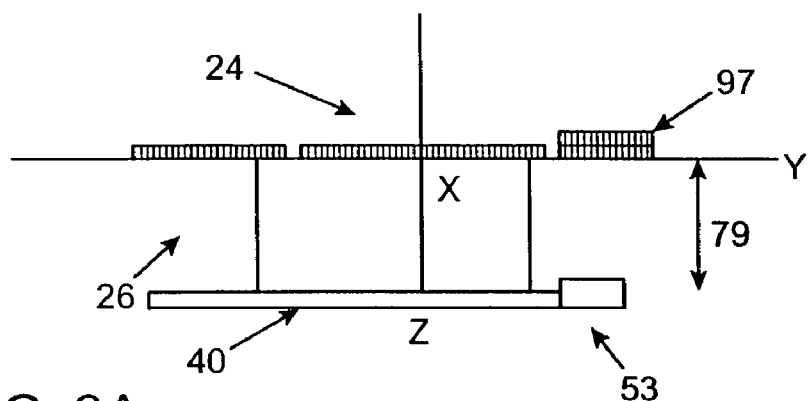
FIG. 8A illustrates an embodiment of the contoured patient seat adjustable along the Z-axis.

FIGS. 8A–8G illustrate a preferred embodiment of the movable patient seat. As shown in FIG. 8A, the patient seat 24 is mounted to base 40 through a gross adjustment mechanism 26. A chair release pedal 53 is typically located at the base. To lock the chair, the operator can press the right side of the pedal. This can prevent the chair from pivoting outward and can prevent the chair main body from being raised. To unlock the chair, the operator can press the left side of the pedal.

Figure 8B:
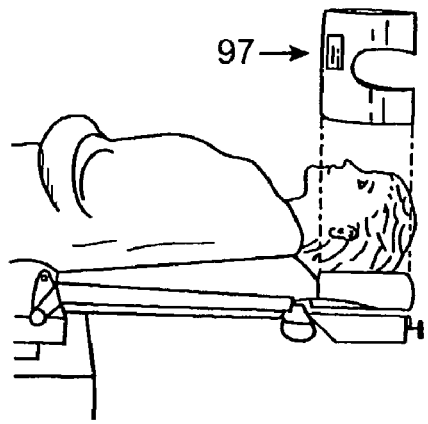
FIG. 8B illustrates an embodiment of the contoured head pillow.

The patient seat or bed typically comprises a head rest 42, a main body 44, and a lower support 46. The head of patient P will be firmly supported by, and preferably restrained by a contoured head rest 97. Preferably, the contoured head rest comprises an adjustable vacuum pillow or cushion which conforms to the patient's head to stabilize the patient's head in position. The pillow can be adjusted for comfort, angle, support and stability. As shown in FIG. 8B, the vacuum pillow 97 is positioned around and under the patient's head P to support the patient. After the patient is placed on the pillow, the operator connects a vacuum pillow suction tubing to the pillow and a suction port. The operator turns on a suction pump with a pillow suction button (not shown), and after about five seconds, the pillow hardens and conforms to the patient's head.

Figure 8C:
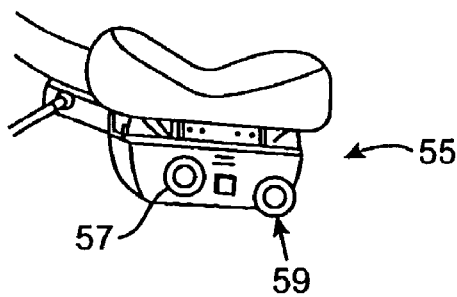
FIG. 8C illustrates a headrest control.
Figure 8D:
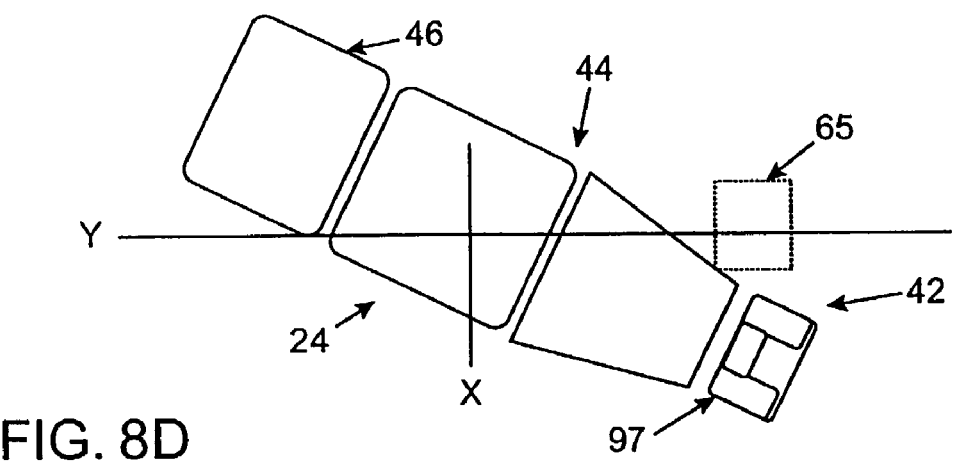
FIG. 8D illustrates a contoured patient seat in a loading position.

As shown in FIG. 8C, chair headrest controls 55 are preferably located underneath the chair headrest to further align the patient's head. Chair headrest controls typically comprise at least two knobs for adjusting the headrest. The head-tilt knob 57, controls the angle of the patient's head. Typically, an operator can turn the knob clockwise to angle the top of the patient's head upward. The neck-tilt knob 59 controls the angle of the patient's neck. Turning of the knob clockwise angles the patient's neck upward.

As shown in FIG. 8A, gross adjustment mechanism 26 is coupled to the control system and is adapted to move the patient seat in at least the X and Y horizontal directions and rotate the seat about at least one of the X, Y, and Z axes. In alternative embodiments, the patient seat is movable in both the horizontal and vertical directions 79 (X, Y, and Z) to axially and laterally align the first optical axis with the laser beam axis (FIG. 8A).

Figure 8E:
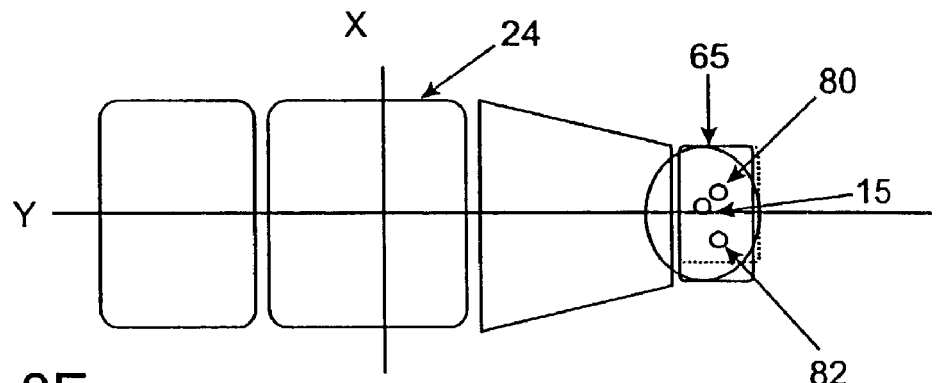
FIG. 8E illustrates a patient seat in a nominal position, substantially aligned with the laser axis, wherein a patient's first eye is within the range of motion of the laser.
Figure 8F:
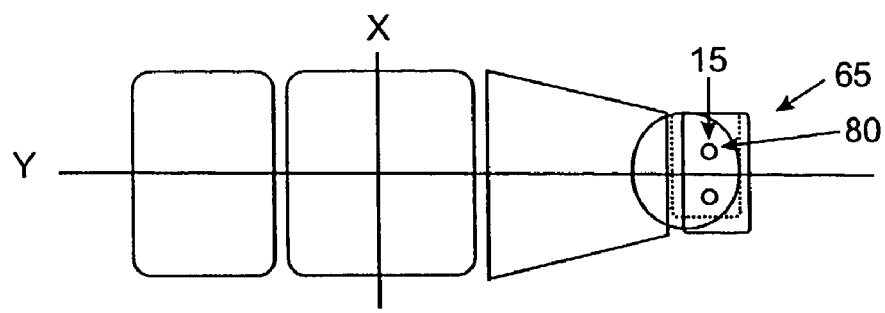
FIG. 8F illustrates a laser axis aligned with a patient's first optical axis.

The control system will typically be programmed to automatically move patient seat 24 from a loading position (FIG. 8D) to a first nominal position (FIG. 8E). Preferably, the first nominal position places the seat in a nominal "X", nominal "Y", and a nominal "Z" position such that the seat is generally near the center of the X, Y, and Z directions and the patient's first optical axis 80 is substantially aligned with the laser beam axis 15. However, the first optical axis will not be always be completely aligned with the laser beam axis 15. As long as the nominal position is within the range of motion 65 of the laser alignment system, the first optical axis 80 can be properly aligned with the laser axis by making adjustments to the fine adjustment mechanism. If fine adjustments are required, the operator can manually adjust the fine adjustment mechanism by actuating the joystick to align the patient's eye with the laser. The operator can manually view the alignment of the laser through the operator interface display 30 or the microscope before the patient is on the seat or bed. Alternatively, the computer control system can be programmed to automatically actuate the fine adjustment mechanism to align the laser beam axis with the first optical axis of the patient's eye. FIG. 8F illustrates the laser axis completely aligned with a patient's first eye.

Figure 8G:
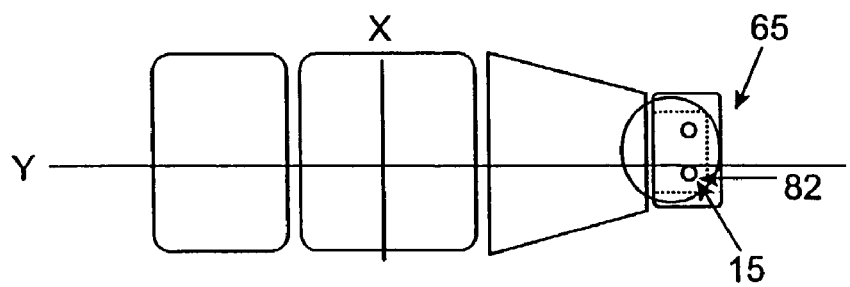
FIG. 8G illustrates the laser axis in a second nominal position, aligned with a patient's second optical axis.

As shown in FIG. 8G, the control system can also be programmed to automatically move to a second nominal position to align a second optical axis 82 (i.e. patient's second eye) with the laser beam axis 15. The control system can be programmed to automatically align the second optical axis with the laser beam axis immediately after treatment of the first eye or to directly align the second optical axis with the laser beam axis. For example, the control system will often be programmed to have the first nominal position align over the patient's right eye. However, in situations where only the left eye is treated, the control system can be programmed in various ways. Alignment can be accomplished by initially moving to the first nominal position (alignment with right eye) and then immediately moving to the second nominal position (alignment with the left eye). Alternatively, the system can be programmed to move directly to the second nominal position. Preferably, the control system can move the patient seat or laser optics to a second nominal position so that the patient's second eye is completely aligned with the laser beam axis. If the eye is not completely aligned with the laser, the operator should not be required to manually realign the patient seat with the gross adjustment mechanism, as the second position will typically be in the range of motion of the fine adjustment mechanism. If adjustments are required, the operator can manually adjust the laser optics, manipulate a computer input device (i.e. joystick) to align the laser axis with the patient's second eye, or allow the control system to automatically align the laser axis with the second optical axis.

Figure 9:
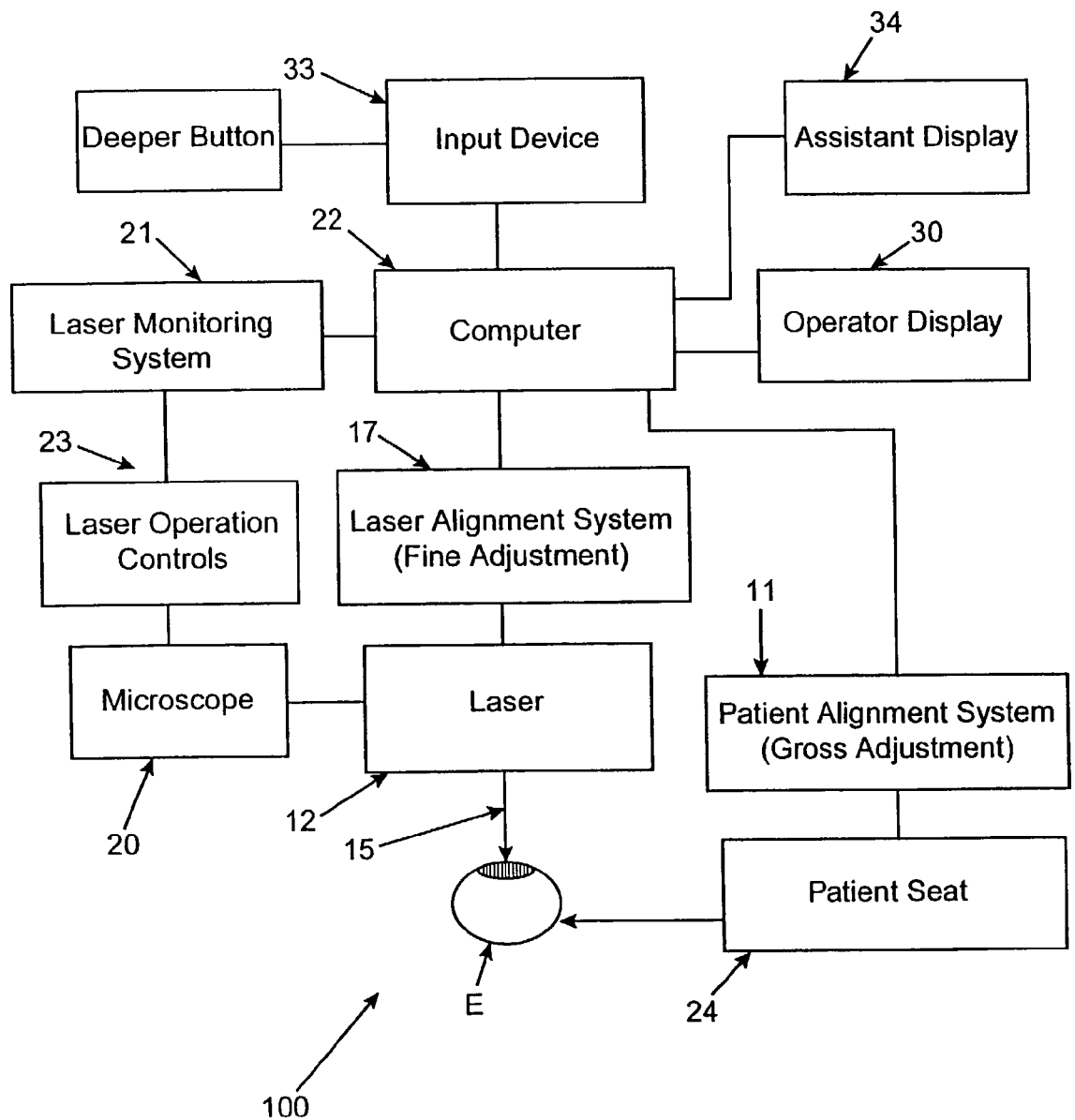
FIG. 9 schematically illustrates an embodiment of the invention.

Referring now to FIG. 9, the computer 22 is coupled to the laser eye system 100 to control the laser eye treatment. Using input devices 33, the operator can manually input the number of laser pulses, the desired patterning of the laser, and the like. The information will generally be shown on the operator interface display 30 and/or the assistant display 34. Typically, a laser monitoring system 21 monitors the eye during the treatment and sends the information to the computer for display on the operator display and/or the assistant display. The laser monitoring system 21 can include of a video camera, sensors, seat position sensors, beam position sensors, or the like. The computer control system will preferably be programmed to display the refractive information, the remaining time, a virtual reticle, and the like.

Figure 10:
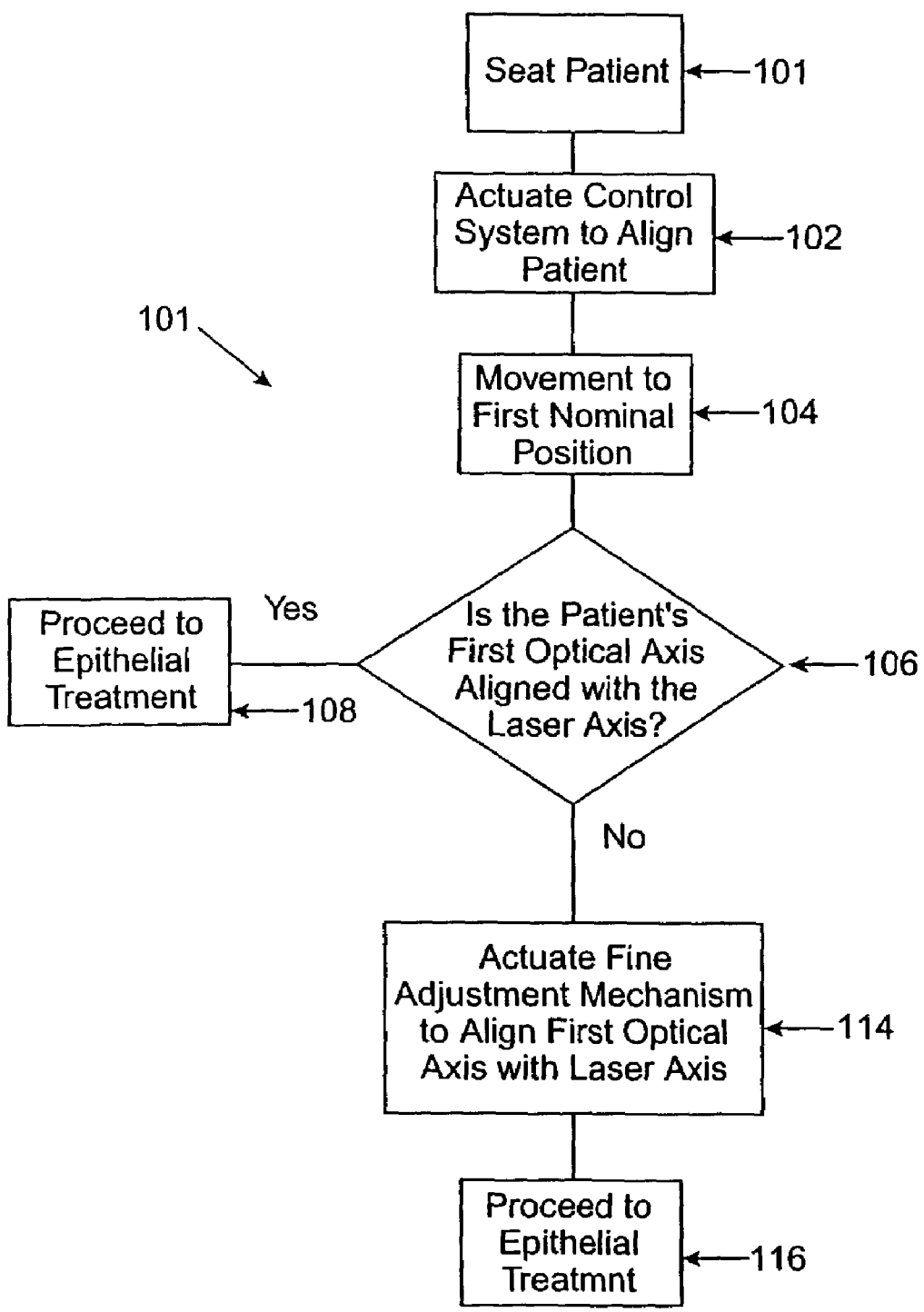
FIG. 10 is a flow chart of the process of aligning a patient with the laser axis.

The operation of a typical procedure will now be described in detail. As illustrated in FIGS. 9 and 10, the patient is initially seated in the patient seat 24 (Step 101). Preferably, the chair is unlocked using the chair release pedal, and the chair can be allowed to rotate outward, upward, or away from the laser. Typically, the chair is moved to a sitting position by pressing a switch on the chair headrest. The chair can then be moved to a reclining position by pressing a switch on the headrest. Using a joystick, the chair can be lowered to its lowest position to allow the patient to be moved beneath the laser. At some point prior to aligning the patient's eye with the laser, the patient's head can be stabilized using a vacuum pillow, as described above.

Next, the operator can actuate the computer control system (Step 102) to send a nominal position control signal to the laser alignment system 17, the patient alignment system 11, or both, to align the patient in a first nominal position (Step 104). Preferably, the operator simply actuates input devices such as a fixed button, a touch screen, or menu selection on the operator display, to move the patient to the first nominal position and align the laser axis with the first optical axis. If the patient's eye is aligned with the laser axis, the operator will proceed to epithelial treatment (Step 108). However, in some situations, the patient will not be completely aligned with the laser axis. Since the patient is within the range of motion of the fine adjustment mechanism, the operator can actuate the control system to send a signal to the fine adjustment mechanism to completely align the laser with the first optical axis (Step 114). Alternatively, the operator can manually align the laser axis with the eye by actuating a joystick. After proper alignment is achieved, the laser can be activated through the laser operation controls 23 to perform the epithelial treatment (Step 116).

Figure 11:
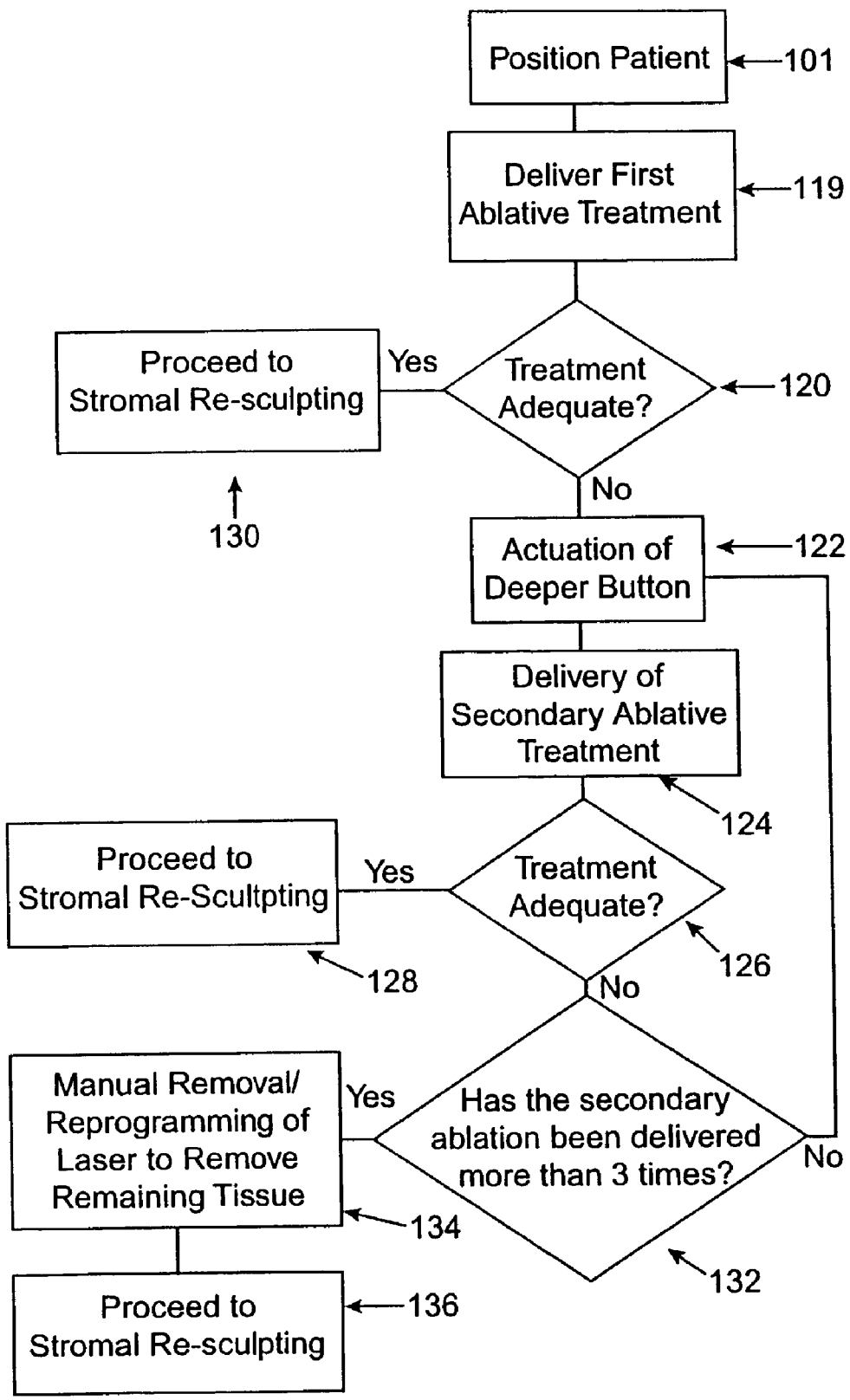
FIG. 11 is a flow chart of the process of ablating the epithelial layer using the deeper button.
Figure 11A:
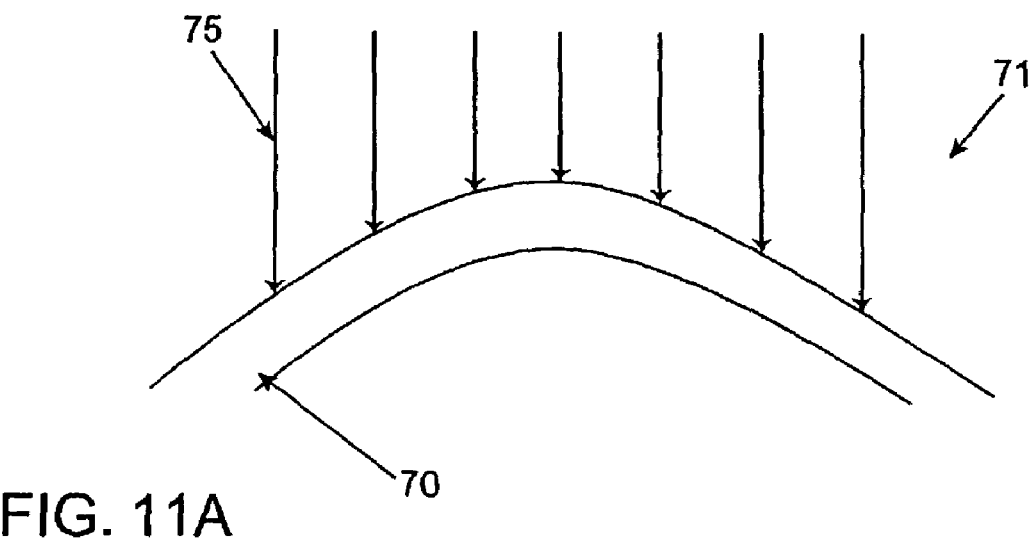
FIG. 11A illustrates a complete epithelial layer in the target region being treated by a first ablative treatment.
Figure 11B:
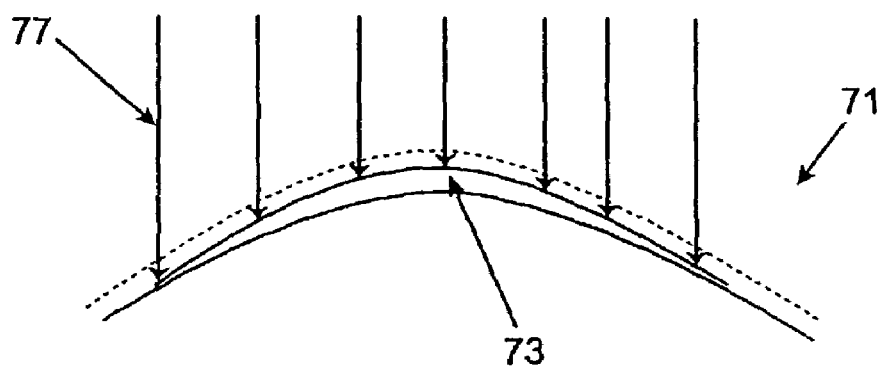
FIG. 11B illustrates an epithelial layer that was not completely removed by the first ablative treatment, which is being treated by a secondary-ablative treatment.

If a photorefractive keratectomy (PRK) is performed, the operator can use the laser operation controls to remove the epithelial layer from the target region prior to shaping the stromal layer. As illustrated in FIGS. 11 and 11A, a pre-programmed first tissue ablative beam 75, typically a uniform beam, can be delivered over the target region of the epithelial layer 70 (Step 119). If the epithelial layer is completely removed, the operator can proceed to stromal re-sculpting (Step 130). However, as illustrated in FIG. 11B, the first ablative treatment 75 often leaves a portion of the epithelial layer 73 in the target region 71. If it is determined that that the first ablative treatment was inadequate (Step 120), the operator can actuate the deeper button (Step 122). Actuation of the deeper button delivers a predetermined secondary ablative treatment 77 to remove the remaining epithelial layer 73 from the target region 71 (Step 124). Typically, each secondary-ablative treatment is an incremental or shorter dosage of the first ablative treatment and is typically programmed to remove between 1 $\mu$m to 15 $\mu$m, and preferably between 5 μm to 10 μm of the epithelial layer. The operator simply presses the deeper button to deliver the secondary ablative treatment. After the delivery of the secondary ablative treatment, the operator can monitor the epithelial layer to determine if the secondary-treatment was adequate (Step 126). If the treatment was adequate, the operator can proceed to the stromal re-sculpting, to correct the vision errors (Steps 128). However, if the secondary treatment was inadequate, the operator can actuate the deeper button to deliver the pre-programmed secondary ablative energy (Step 122). In a preferred embodiment, the control system can be programmed to limit the amount of secondary-ablative treatment to that of approximately 25 μm. Preferably, this is achieved by limiting the amount of times the deeper button can be actuated. For example, the computer can be programmed to allow the operator to press the deeper button a 3 times (Step 132) before having to manually re-program the laser to remove the remaining epithelial tissue (Step 134). This safety feature can help avoid the inadvertent ablation of the underlying stromal layer.

Some embodiments of the system allow the operator to program the power, patterning of the laser, time of ablation, depth of epithelial tissue to be removed, and the like. For example, if the first ablative treatment removes 35 μm of the epithelial layer, and the operator presses the deeper button and removes 10 μm of the epithelial layer, the operator can program the next ablative energy to ablate between 1–5 μm. Alternatively, the operator can preprogram the deeper button to deliver only 5 μm for every secondary ablative treatment. Moreover, the control system can be programmed to reduce each subsequent secondary ablative treatments. For example, the initial secondary ablative treatment can be programmed to ablate 10 μm of the epithelial layer, the subsequent treatments can be programmed to ablate 5 μm of the epithelial layer, and so forth. Preferably, the control system can monitor the ablation of the epithelial layer and display on the operator display the progress of the ablation.

Figure 12:
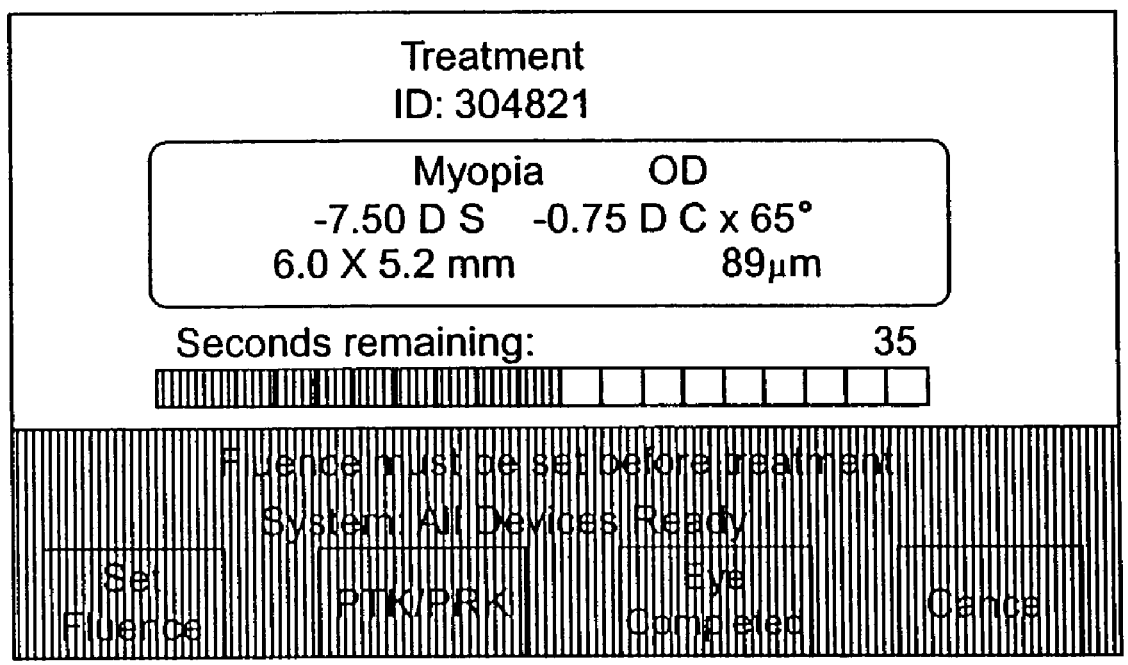
FIG. 12 shows a touch screen having a second sample treatment screen after the epithelial layer of the target region has been removed.

Once the epithelial layer has been completely removed the operator can proceed to the stromal re-sculpting. Typically, the control system will display a treatment screen having refractive information, treatment time, or the like. A sample treatment screen is shown in FIG. 12.

While the above is a complete description of the preferred embodiments of the invention, various alternatives, modifications, and equivalents may be used. Therefore, the above description should not be taken as limiting the scope of the invention which is defined by the appended claims.

What is claimed is:

1. A laser refractive system comprising:
a laser comprising laser delivery optics, the laser produces a laser beam having a longitudinal axis;
a patient seat contoured to support a patient in a patient position so that first and second eyes of the patient are near first and second nominal optical axes, respectively; and
a patient alignment system coupling the seat to the laser, the alignment system moving at least one of the patient seat or the laser delivery optics in response to a nominal position signal so that the laser beam longitudinal axis is substantially aligned with the first nominal optical axis.

2. A laser refractive system as recited in claim 1 wherein the alignment system is configured to automatically move at least one of the patient seat and the laser delivery optics to a second nominal position in response to a second nominal position signal so that the laser beam longitudinal axis is substantially aligned with the second nominal optical axis.

3. A laser refractive system as recited in claim 1 wherein the patient seat comprises an adjustable vacuum pillow that is adjustably configured to conform to patient's head, wherein the adjustable vacuum pillow is coupled to a vacuum source with a tubing.

4. A system as recited in claim 1, wherein:
the patient seat is movable along at least X and Y horizontal directions; and
the alignment system includes a control system configured to automatically position the patient seat at the first nominal position in the X and Y directions.

5. A laser refractive system as recited in claim 1 wherein the patient seat comprises an adjustable vacuum pillow that is adjustably configured to conform to patient's head, wherein the adjustable vacuum pillow is coupled to a vacuum source with a tubing.

6. A system as recited in claim 1, further comprising a computer program having a tangible medium and computer-readable code, wherein the control system uses the computer program to automatically align the patients second eye with the laser beam longitudinal axis.

7. A system as recited in claim 1, wherein the first nominal position is substantially near a center of the X and Y horizontal directions.

8. A system as recited in claim 7 wherein the patient seat is movable along the X, Y, and Z directions, wherein the control system is configured to automatically position the seat at a nominal position of the X, Y, and Z directions.

9. A system as recited in claim 1, the alignment system further comprising a fine adjustment mechanism for aligning the laser beam with the patient's first eye, wherein the fine adjustment mechanism moves the patient seat or a laser delivery optics.

10. A system as recited in claim 9, wherein the fine adjustment mechanism comprises an activating motor, wherein the activating motor is coupled to the patient seat and the control system such that the activating motor moves the patient seat in response to a signal from the control system.

11. A system as recited in claim 3, wherein the activating motor moves the patient seat in response to the signal that is generated from manual actuation of an input device.

12. A system as recited in claim 9, wherein the fine adjustment mechanism comprises an activating motor, wherein the activating motor is coupled to the laser delivery optics and the control system, such that the activating motor moves the laser delivery optics in response to a signal from a control system.

13. A system as recited in claim 12, wherein the activating moves the laser delivery optics in response to a signal that is generated from manual actuation of an input device.

14. A system as recited in claim 9, wherein the alignment system further comprises a gross adjustment mechanism that is independent of the fine adjustment mechanism, wherein the gross adjustment mechanism substantially aligns the first nominal optical axis with the laser beam longitudinal axis by moving the patient seat.

15. A system as recited in claim 14, wherein the gross adjustment mechanism comprises an activating motor, such that the activating motor moves the patient seat in response to the nominal position signal from the control system.

16. A system as recited in claim 15, wherein the activating motor moves the seat in response to the nominal position signal that is generated from manual actuation of an input device.

17. A system as recited in claim 14, wherein the control system actuates the gross adjustment mechanism, the fine adjustment mechanism, or both, to automatically substantially align a second eye of the patient with the laser beam longitudinal axis.

18. A system as recited in claim 17, wherein the control system substantially aligns the second eye of the patient with the laser beam longitudinal axis after the first eye has been treated with the laser.

19. A system as recited in claim 18, wherein the control system substantially aligns the second eye with the laser axis in response to an input into the control system.

* * * * *